US010821081B2

(12) United States Patent
Yaniv et al.

(10) Patent No.: US 10,821,081 B2
(45) Date of Patent: Nov. 3, 2020

(54) INSTRUMENT FOR SKIN TREATMENT (71) Applicants: Zvi Yaniv, Austin, TX (US); Igor Alexander Goldman, Austin, TX (US)

(72) Inventors: Zvi Yaniv, Austin, TX (US); Igor Alexander Goldman, Austin, TX (US)

(73) Assignee: Nanobubbling, LLC, Austin, TX (US)

( * ) Notice: Subject to any disclaimer, the term of this patent is extended or adjusted under 35 U.S.C. 154(b) by 71 days.

(21) Appl. No.: 15/850,362

(22) Filed: Dec. 21, 2017

(65) Prior Publication Data
US 2018/0177737 A1 Jun. 28, 2018

Related U.S. Application Data (60) Provisional application No. 62/437,920, filed on Dec. 22, 2016, provisional application No. 62/490,800, filed on Apr. 27, 2017, provisional application No. 62/551,356, filed on Aug. 29, 2017.

(51) Int. Cl.
*A61K 9/00* (2006.01)
*A61K 33/00* (2006.01)
*B01F 3/04* (2006.01)
*B01F 5/04* (2006.01)
*A61K 9/08* (2006.01)
*A61K 9/50* (2006.01)

(52) U.S. Cl.
CPC .............. *A61K 9/50* (2013.01); *A61K 9/0014* (2013.01); *A61K 9/08* (2013.01); *A61K 33/00* (2013.01); *B01F 3/04248* (2013.01); *B01F 3/04503* (2013.01); *B01F 5/0465* (2013.01); *B01F 2003/04858* (2013.01); *B01F 2003/04879* (2013.01); *B01F 2003/04893* (2013.01); *B01F 2215/0034* (2013.01); *B01F 2215/0495* (2013.01)

(58) Field of Classification Search
CPC ........ A61K 33/00; A61K 9/0014; A61K 9/08; A61K 9/0019; A61K 9/0051; A61K 9/06; A61K 9/50; B01F 2003/04858; B01F 2003/04879; B01F 2003/04893; B01F 3/04248; B01F 3/04503; B01F 5/0465; B01F 2215/0034; B01F 2215/0495; B01F 2003/0439; B01F 3/04262
See application file for complete search history.

(56) References Cited

U.S. PATENT DOCUMENTS

| | | | | |
|---|---|---|---|---|
| 5,578,310 A | * | 11/1996 | M'Timkulu | ............ A61K 9/006 424/401 |
| 8,481,077 B2 | | 7/2013 | Kheir | |
| 8,597,689 B2 | * | 12/2013 | Archambeau | ........ A61K 9/0048 424/613 |
| 2006/0284325 A1 | * | 12/2006 | Kohama | ............. B01F 3/04262 261/122.1 |

FOREIGN PATENT DOCUMENTS

| WO | 2009043031 A2 | 4/2009 |
|---|---|---|
| WO | 2017172887 A1 | 10/2017 |

OTHER PUBLICATIONS

Anzaikantetsu MCS Division, Nanobubles technology anzaikantetsu, 9 pages, http://anzaimcs.com/en/main/examplenanobubble.html, downloaded Dec. 12, 2016.
Frangez, I. et al., "Use of Transcutaneous Application of CO2 in Diabetic Foot Pathology," Clinical Research on Foot & Ankle, vol. 5, issue 2, Apr. 19, 2017, 2 pages.
Hashimoto, M. et al., "Decrease in heart rates by artificial CO2 hot spring bathing is inhibited by β1-adrenoceptor blockage in anesthetized rats," J. Appl. Physiol., vol. 96, Aug. 29, 2003, pp. 226-232, www.jap.org.
Hayashi, H. et al., "Immersing Feet in Carbon Dioxide-enriched Water Prevents Expansion and Formation of Ischemic Ulcers after Surgical Revascularization in Diabetic Patients with Critical Limb Ischemia," Annals of Vascular Diseases, vol. 1, No. 2, Oct. 24, 2008, pp. 111-117.
Maeda, M. et al., "The Effects of High Concentration Artificial $CO_2$ Warm Water Bathing for Arteriosclerotic Obstruction (ASO)," Japan Hot Spring Climate Physical Medicine Society Magazine, vol. 66, No. 3, pp. 156-164.
Nanobubbles (ultrafine bubbles), Water structure and science, http://www1.lsbu.ac.uk/water/nanobubble.html, 9 pages, Dec. 12, 2016.
National Institutes of Health, U.S. Department of Health and Human Services, "Diabetic Neuropathies: The Nerve Damage of Diabetes," Nov. 2013, 12 pages.
Parker, J. et al., "Bubbles, Cavities, and the Long-Ranged Attraction between Hydrophobic Surfaces," J. Phys. Chem., vol. 98, No. 34, May 26, 1994, pp. 8468-8480.
Shalan, N. et al., "Effect of Carbon Dioxide Therapy on Diabetic Foot Ulcer," Journal of Diabetes Mellitus, Nov. 5, 2015, vol. 5, pp. 284-289.
Stücker, M. et al., "The cutaneous uptake of atmospheric oxygen contributes significantly to the oxygen supply of human dermis and epidermis," Journal of Physiology, 2002, 538.3, pp. 985-994.
Sunnen, G., M.D., "Diabetic Wound Management: A Key Ingredient is Missing," Mar. 2007, 10 pages.
Tappia, P. et al., "Evaluation of the clinical utility, efficacy and safety of a novel medical device for the treatment of foot ulcers: Rationale and design of the carbothera trial," Curr. Res. Cardiol., vol. 3, No. 4, Aug. 18, 2016, pp. 117-120.
Weijs, J. et al., "Why surface nanobubbles live for hours," Nov. 14, 2012, 5 pages.

(Continued)

*Primary Examiner* — Michael B. Pallay
(74) *Attorney, Agent, or Firm* — Kelly Kordzik; Matheson Keys & Kordzik PLLC (57) ABSTRACT An apparatus configured to result in a penetration of one or more gasses into a dermis of biological skin, wherein the apparatus includes a fluid reservoir configured to contain an amount of a liquid in contact with a portion of a person's skin, and a nanobubble generator configured to inject nanobubbles into the liquid, wherein the nanobubbles contain the one or more gasses. The contact of the liquid containing the nanobubbles with the person's skin results in a cutaneous uptake of a gas contained in the nanobubbies into the person's skin, which may be beneficial in treating an ailment, such as diabetic peripheral neuropathy.

16 Claims, 6 Drawing Sheets

(56) References Cited

OTHER PUBLICATIONS

Bisazza et al., "Microbubble-Mediated Oxygen Delivery to Hypoxic Tissues as a New Therapeutic Device," $30^{th}$ Annual International IEEE EMBS Conference, Vancouver, BC, , pp. 2067-2070, Aug. 20-24, 2008.

Cavalli et al., "Preparation and characterization of dextran nanobubbles for oxygen delivery," International Journal of Pharmaceutics, vol. 381, pp. 160-165, Jul. 17, 2009.

Roe et al, "Topical Dissolved Oxygen Penetrates Skin: Model and Method," Journal of Surgical Research, vol. 159, pp. e29-e36, May 28, 2009.

\* cited by examiner

INSTRUMENT FOR SKIN TREATMENT

This application claims priority to U.S. provisional patent applications Ser. Nos. 62/437,920, 62/490,800, and 62/551,356, which are each hereby incorporated by reference herein.

TECHNICAL FIELD

The present invention relates in general to the generation of gas nanobubbles, and in particular, to therapeutic applications utilizing such gas nanobubbles.

BACKGROUND

Peripheral Neuropathy, also referred to as Distal Symmetric Neuropathy, is nerve damage occurring, for example, in the arms and legs. Feet and legs are likely to be affected before hands and arms. Many people with diabetes have signs of neuropathy (see, e.g., "Diabetic Neuropathies: The Nerve Damage of Diabetes," National Institute of Diabetes and Digestive and Kidney Diseases, 12 pages, which is hereby incorporated by reference herein). In fact, one of the most prevalent forms of peripheral neuropathy is diabetic neuropathy. Diabetic neuropathy is caused by damage to nerves and blood vessels. Prolonged exposure to high blood sugar damages delicate nerve fibers causing diabetic neuropathy; medically, one can say that the neuropathy is a result of complex interactions between nerves and blood vessels. Basically, high blood sugar interferes with the ability of the nerves to transmit signals. It also weakens the walls of the small blood vessels (capillaries) that supply the nerves with oxygen and nutrients.

In the majority of cases, the diabetic neuropathy begins at the soles of the feet, and is a form of peripheral neuropathy. Symptoms can range from numbness, tingling, "prickly" sensations, and sometimes burning pain. An estimated 20 million people in the United States have some form of peripheral neuropathy.

In the case of diabetic neuropathy, the sensory nerves at the bottom of the feet no longer transmit the feeling of a light, touch or the pain from a cut. As a result, many diabetic persons cut themselves on the bottom of the feet, but do not feel the pain, with the resulting infections contributing to a high rate of lower limb amputations.

There are no proven medicines or procedures to alleviate the suffering of the patients or reversal of the disease. One instrument that is currently utilized is the hyperbaric oxygen chamber (e.g., see, "Diabetic Foot Ulcer Treatment Using Hyperbaric Oxygen Therapy Guide," Sechrist Industries, Inc., copyright 2008, 13 pages, which is hereby incorporated by reference herein). However, this is a very expensive instrument (for example, in Austin, Tex., there are only three such available instruments), and basically the patient is introduced into a closed cell with pressurized oxygen even if only the feet (or hands) are suffering from peripheral neuropathy. As a result, this treatment is very expensive, cumbersome, and is not a very efficient solution.

DETAILED DESCRIPTION

As previously disclosed, diabetic neuropathies are a family of nerve disorders caused by diabetes. Over time, people with diabetes, develop nerve damage throughout the body. In general, the symptoms include pain, tingling, or numbness in the feet, hands, arms, and/or legs. About 60-70% of people with diabetes have some form of neuropathy and one of the most common is peripheral neuropathy of the bottom of the feet. The causes of diabetic neuropathy can be a combination of factors that include a long duration of diabetes, neurovascular factors leading to damage of the blood vessels that early oxygen and nutrients to the nerves, autoimmune factors, inherited traits, etc. The most common type of diabetic neuropathy causes pain or loss of feeling in the toes, feet, legs, hands, and/or arms. In the majority of the cases, it begins in the feet and then progresses to the hands.

The biggest problem in the case of diabetic peripheral neuropathy is that the blood vessels that supply oxygen and nutrients to the nerves in the extremities narrow, and as a result, oxygen and nutrients are not delivered to the peripheral nerves, Which eventually die. Thus, a good solution would be able to alter the situation of a patient such that the blood vessels that supply the nerves in the extremities are enlarged, allowing greater flow of blood, and additionally increasing the concentration of oxygen at these locations.

It is known that carbonated springs, which are typically hot springs with a high concentration of carbon dioxide ("$CO_2$"), contribute to create beautiful and healthy skin. The effect of the $CO_2$ is the expanding of blood vessels, and as a result naturally improving the blood flow (see, e.g., H. Hayashi et al., "Immersing Feet in Carbon Dioxide-enriched Water Prevents Expansion and Formation of Ischemic Ulcers after Surgical Revascularization in Diabetic Patients with Critical Limb Ischemia," Ann Vase Dis., 1(2), pp. 111-117, Oct. 24, 2008; M. Hashimoto et al., "Decrease in heart rates by artificial $CO_2$ hot spring bathing is inhibited by $\beta_1$-adrenoceptor blockade in anesthetized rats," J Appl Physiol, 96, pp. 226-232, Aug. 29, 2003; and M. Maeda et al., "The Effects of High Concentration Artificial $CO_2$ Warm Water Bathing for Arteriosclerotic Obstruction (ASO)," The Journal of The Japanese Society of Balneology, Climatology and Physical Medicine, Volume 66 issue 3, pp. 156-164, Apr. 30, 2010, which are all hereby incorporated by reference herein). The $CO_2$ penetrates through the skin into the capillaries, causing the blood vessels to dilate, and frees up more oxygen that has been bound to the hemogoblin (also referred to as the Bohr Effect) (e.g., see, N. Nishimura et al., "Effects of repeated carbon dioxide-rich water bathing on core temperature, cutaneous blood flow and thermal sensation," Eur. J. Appl. Physiol. 87, pp. 337-342, Jun. 7, 2002, which is hereby incorporated by reference herein).

Figure 1:
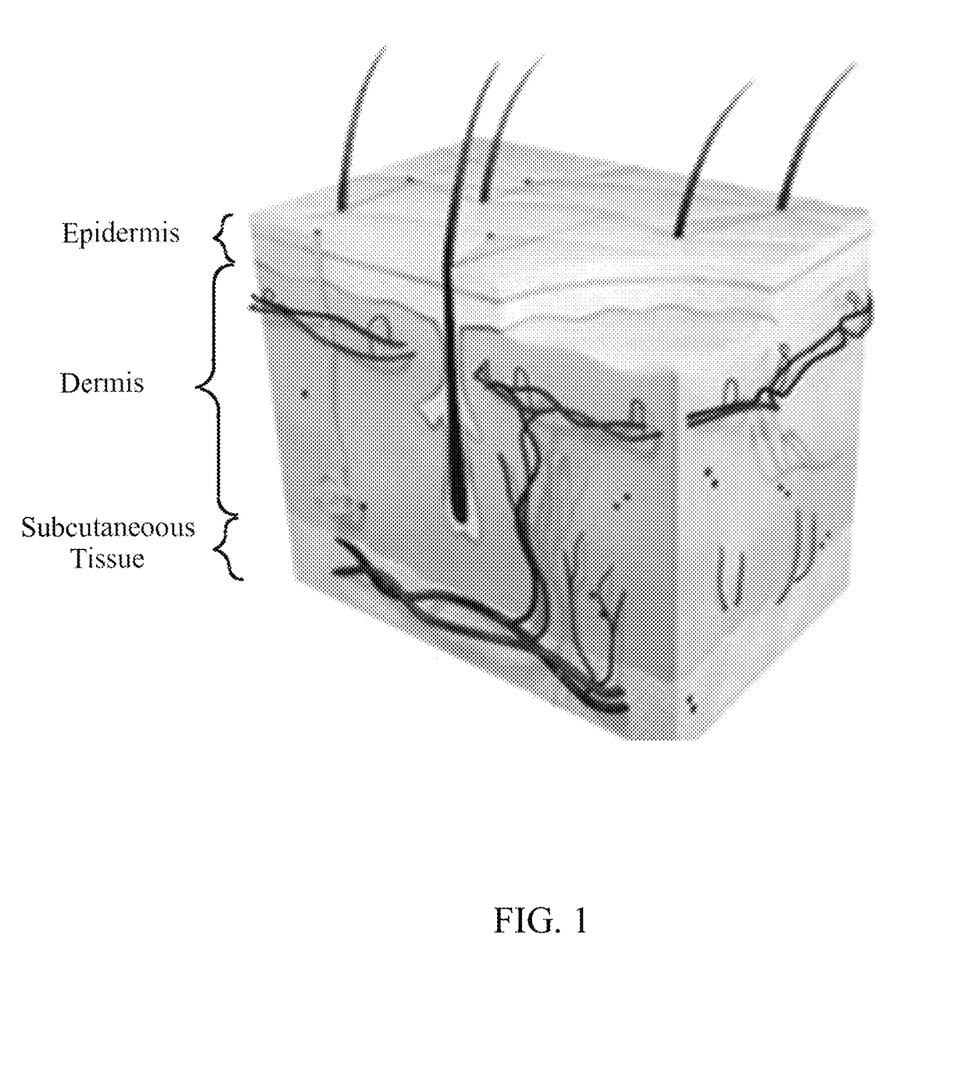
FIG. 1 illustrates a diagram of the dermis and epidermis of biological skin.

Referring to the diagram of the dermis and epidermis in FIG. 1, it has also been shown that a cutaneous uptake of atmospheric oxygen contributes significantly to the oxygen supply of the human dermis and epidermis (see, M. Stucker et al., "The cutaneous uptake of atmospheric oxygen contributes significantly to the oxygen supply of human dermis and epidermis," Journal of Physiology (2002), 538.3, pp. 985-994, Feb. 1, 2002, which is hereby incorporated by reference herein). In a study, it was shown that under normal conditions, atmospheric oxygen can supply the upper skin layers at a depth of 0.25-0.4 millimeters. As a result, if one can supply oxygen that is presented to the skin in the form of nanobubbles (e.g., on the order of tenths of a nanometer in diameter (e.g., less than 1 micron), which is compatible with the typical dimensions of skin pores (average diameter 50 µm)) the oxygen can be directly permeable to the nerves in the dermis (e.g., see, M. Stucker et al. previously referenced and D. Ladizinsky et al., "New insights into oxygen therapy for wound healing," Wounds, 22(12), pp. 294-300, December, 2010, which are hereby incorporated by reference herein). Furthermore, oleic acids, which can be topically applied, are known to increase the diameter of skin pores.

As will be further disclosed herein, embodiments of the present invention supply $CO_2$ and/or oxygen directly to the areas in the skin affected by diabetic peripheral neuropathy, and more specifically $CO_2$ and/or oxygen nanobubbles, which can easily penetrate into the skin pores and penetrate deep into the dermis to dilate the blood vessels that supply the peripheral nerves, while also supplying additional oxygen directly to the nerves. It is known that while oxygen has antibacterial and antimicrobial properties, ozone ($O_3$) is even more effective; thus, nanobubbles containing ozone can also be supplied to the skin as disclosed herein. Furthermore, embodiments of the present invention can also be utilized in a similar approach, for wound irrigation, and even for cosmetic reasons, such as beautification of the skin.

Figure 2:
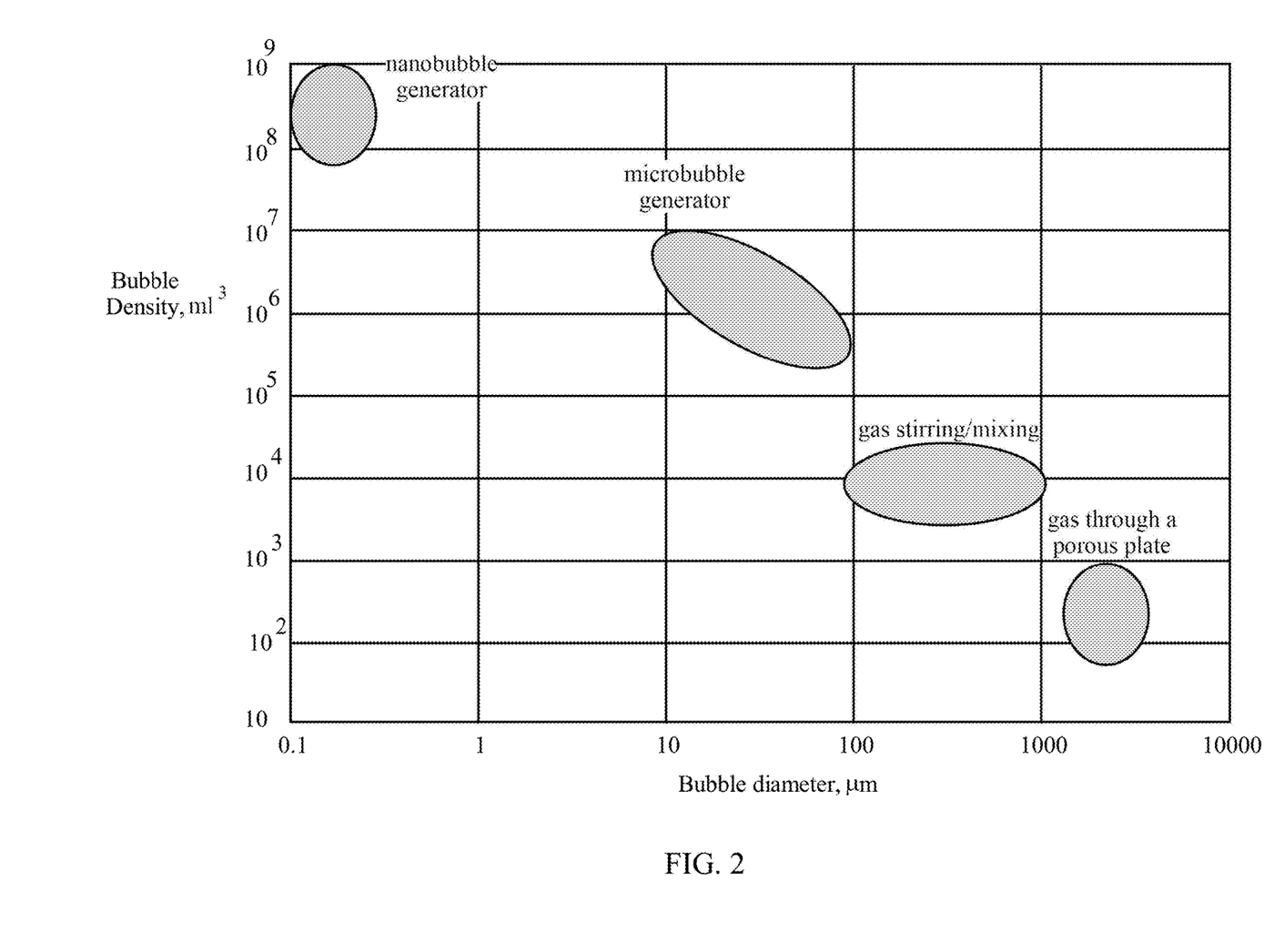
FIG. 2 shows a graph of bubble density and diameter.

Referring to FIG. 2, nanobubbles generated in accordance with embodiments of the present invention are gas-filled bubbles within a liquid (e.g., water, oil, saline, gels, lotions, ointments, etc.) having a diameter less than 100 nm. Some define nanobubbles as bubbles in a liquid with a diameter smaller than 1 µm and larger than 1 nm. Other embodiments of the present invention may utilize nanobubbles generated in materials, such as gels and lotions, having viscosities less than 100,000 cP. Furthermore, creams with viscosities less than 600,000 cP can also be injected/infused with nanobubbles for use in embodiments of the present invention. Additionally, ointments having higher viscosities than 600,000 cP can be infused injected with nanobubbles by increasing their temperature in order to lower their viscosity.

Each bubble is surrounded by an interface with different properties than the bulk liquid. Bubbles with a diameter less than 1 micron are referred to herein as "ultra-fine bubbles" ("UFB"), which include the family of nanobubbles as defined above.

The surface area of bubbles is inverse proportional to the bubble diameter. As an example, a 100 nm bubble in a 1 ml liquid can contain about $2 \times 10^{15}$ bubbles, with a surface area that is 1,000 times (240 m$^2$) more than the surface area of a 1 mm bubble in the same volume of liquid (e.g., $2 \times 10^6$ bubbles with a total surface area of 0.24 m$^2$). "Fine bubbles" have inflexible surfaces (for example, as in high pressure balloons) that limit distortions, while large bubbles have flexible surfaces (for example, as in low pressure balloons) and can break up relatively easily.

The buoyancy of large bubbles causes them to rise to the surface of aqueous liquids. Although the behavior of bubbles in aqueous liquids is complex, the rising rate of bubbles can be approximated using Stokes's equation:

$$R = \rho g d^2 / 18\mu$$

where R represents the rise rate, ρ represents the density, g represents gravity, d represents the bubble diameter, and µ represents the dynamic viscosity (Pa×s). Accordingly, a 25 µm diameter bubble will rise at a rate of ~2.3 cm/min, while nanobubbles will rise much more slowly than their Brownian motion. Since nanobubbles are dominated by Brownian motion rather than behaving according to Stoke's equation, they diffuse into the water with minimal or no buoyancy effects.

The generation of nanobubbles can be accomplished by vigorously mixing a combination of gas and a liquid, which will generally produce bubbles with a wide range of diameters. Referring to FIG. 2, smaller bubbles when generated have a higher concentration than larger bubbles. Nanobubbles are generated at the highest density (e.g., see, M. Chaplin, "Water Structure and Science," downloaded from the Internet, 2007 (last updated on Nov. 9, 2017), which is hereby incorporated by reference herein).

The degree of saturation next to a bubble depends on the gas pressure within the bubble. The energy cost of bubble formation depends on the interfacial area and is governed by the bubble's surface tension. Smaller bubbles have higher internal pressure and release gas to dissolve under pressure into an under-saturated liquid. Larger bubbles grow by taking up gas from a super saturated liquid. As a result, small bubbles shrink and large bubbles grow. As bubbles rise, the pressure on them drops, and consequently they enlarge and rise faster. Nanobubbles rise much slower due to low buoyancy and their random Brownian motion. The overall behavior of nanobubbles is complex due to the shrinking effects that are in competition to the effect of buoyancy. Consequently nanobubbles have a tendency to diffuse into the liquid; they do not rise and they never accumulate in the upper part of the liquid.

Additionally, the electrostatic interaction between nanobubbles can be large enough to avoid coalescence. Electrostatic interaction will slow any rise even more. The zeta potential is generally negative and mostly independent of the bubble diameter. The zeta potential depends strongly on the pH and the dissolved salt concentrations whereby increased ionic strength reduces zeta potential. As all the bubbles are similarly charged, their coalescence is discouraged. The zeta potential of a bubble can be determined from its horizontal velocity in a horizontal electric field:

$$v = \zeta \epsilon / \mu$$

where $\zeta$ represents the zeta potential, $\epsilon$ represents the permittivity, and µ represents the dynamic viscosity.

Figure 6:
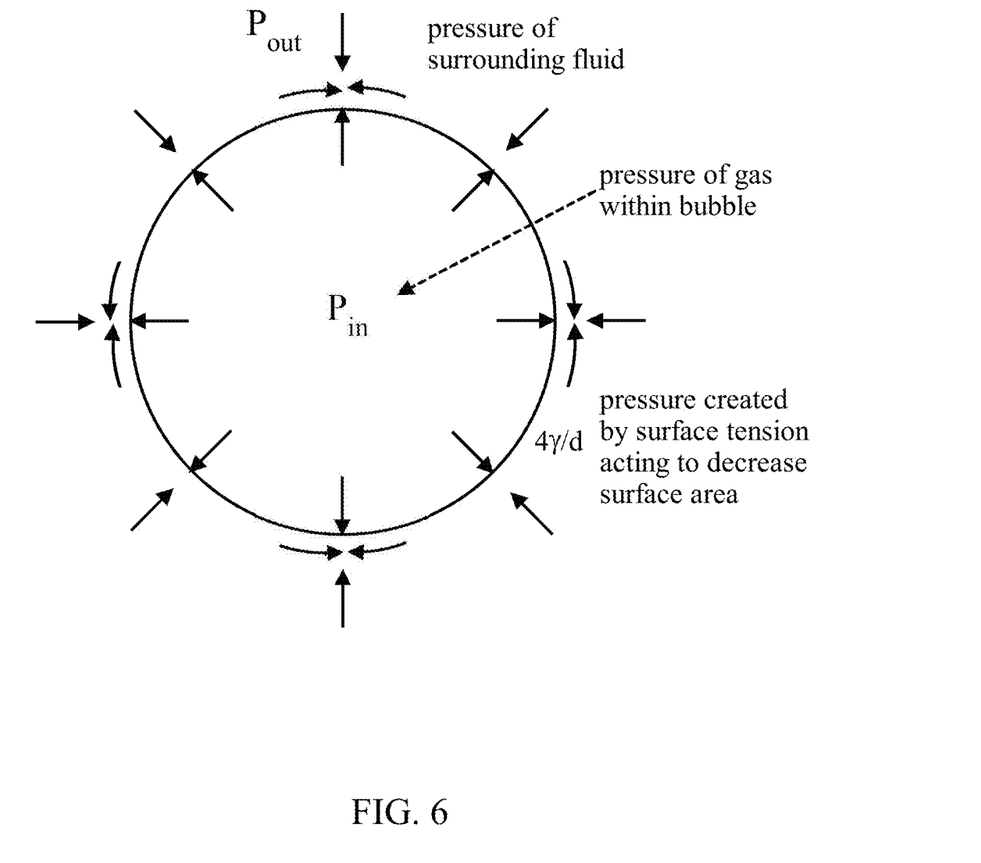
FIG. 6 depicts a demonstration of the Laplace equation and nanobubble stability.

Referring to FIG. 6, according to the Laplace equation, the following is the pressure inside a gas bubble for soluble gasses:

$$P_{in} = P_{out} + 4\gamma/d$$

where $P_{in}$ represents internal pressure, $P_{out}$ represents external pressure, γ represents surface tension, and d represents bubble diameter. The expression 4γ/d is defined as the excess pressure.

The controversy over nanobubbles existence is based on the fact that as the diameter of the bubble is in the range of nanometers, the internal pressure will be very high, significantly reducing their lifespan. By reducing the surface tension utilizing a surface-active material (e.g., a surfactant), the excess pressure can be lowered in order to stabilize the bubbles. The concentration of surface-active agents may also be used to regulate the bubble size. Such coated UFBs are used in the medical field as ultrasound contrast agents and for targeted drug delivery.

However, the Laplace equation may not hold at small diameters such as nanobubbles. For nanobubbles, the calculated internal gas pressure should cause an almost instantaneously dissolution, but as nanobubbles are now known to exist for long periods, the existing basic theories may be insufficient.

Nanobubbles Controversy

The reason for the controversy is simple in that nanobubbles should not exist according to known principals of physics. Instead, they should vanish in an instant, yet experiments show clearing that they exist and can defiantly persist for weeks. Nanobubbles were first proposed in 1994 by Phil Attard and his colleagues (see, P. Attard et al., "Bubbles, Cavities, and the Long-Ranged Attraction between Hydrophobic Surfaces," J. Phys. Chem., vol. 98, no. 34, pp. 8468-8480, August 1994). Valuable experimental results were provided by Kyoto University in Japan and the Chinese Academy of Sciences in Shanghai (see, S-T. Lou et al., "Nanobubbles on solid surface imaged by atomic force microscopy," J. Vac. Sci Technol., vol. 18, no. 5, pp. 2573-2575, October 2000; and N. Ishida et al., "Nano Bubbles on a Hydrophobic Surface in Water Observed by Tapping-Mode Atomic Force Microscopy," Langmuir, vol. 16, no. 16, pp. 6377-6380, Jul. 6, 2000). Despite the proof of the existence of nanobubbles, many believe that their longevity does not make any sense. Stability requires mechanical equilibrium, meaning that $P_{in}$ must balance $P_{out}$. The Laplace equation shows that for a nanobubble, the $P_{in}$ should be very large, meaning that the gas in the bubble should rapidly diffuse into the water in less than a millisecond. Yet, experimental proof shows that they are visible for hours, days, and even longer. Many theoretical explanations were given (for example, see, M. P. Brenner et al., "Dynamic Equilibrium Mechanism for Surface Nanobubble Stabilization," Phys. Rev, Lett., vol. 101, no. 21, 214505, Nov. 21, 2008), and some have suggested that it is possible that the Laplace equation breaks down at nanometer scales (see, J. R. T. Seddon et al., "A Deliberation on Nanobubbles at Surfaces and in Bulk," ChemPhysChem, vol. 13, pp. 2179-2187, Feb. 29, 2012; and J. W. Weijs et al., "Why surface nanobubbles live for hours," Phys Rev Lett., vol. 110, Jan. 31, 2013, 5 pages). At present, it is still somewhat a "mystery" why nanobubbles persist. Nevertheless, in contrast to previous theoretical views, there is now much evidence that gas-filled nanobubbles can exist for significant periods of time in aqueous liquids.

Although nanobubbles are smaller than the wavelength of light and therefore too small to be visible to the naked eye or standard microscope, they can be visualized by backscattering of the light from a laser pointer. Nanobubbles can be also observed by dynamic light scattering ("DLS"). The fluctuation of the scattering of laser light travelling through the sample liquid is due to the Brownian motion whereby larger bubbles are showing greater scattering but lower fluctuations. Analysis of the total signal gives both the concentration and size distribution of the nanobubbles. Other detection methods include cryoelectron microscopy ("cryo-EM") and resonant mass measurement.

Figure 3:
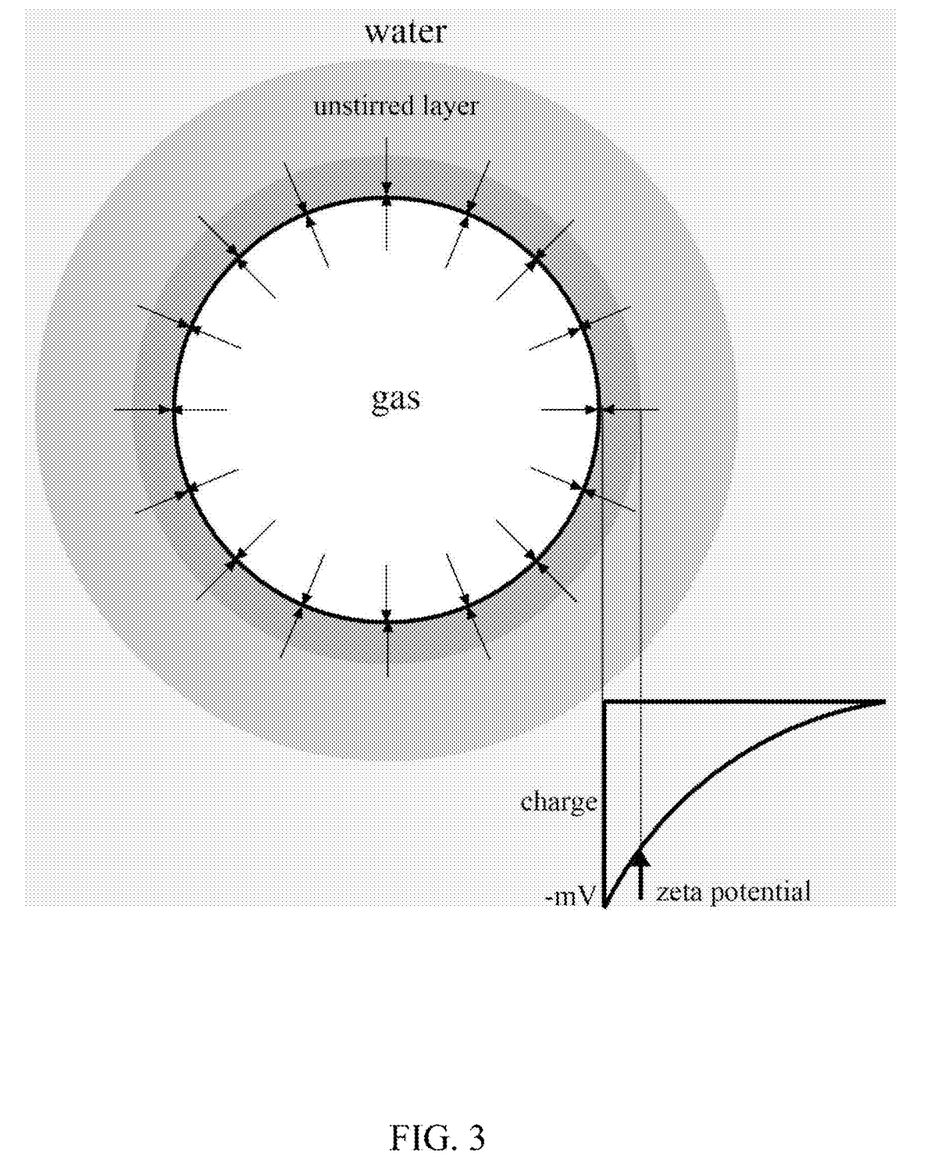
FIG. 3 illustrates a schematic pertaining to the charging of gas nanobubbles.

Referring to FIG. 3, a likely reason for the long-lived presence of nanobubbles is that the gas/liquid interfaces of the nanobubbles are charged. This charge introduces an opposing force to the surface tension, slowing or preventing dissipation of the nanobubbles. The presence of charges at the interface reduces the internal pressure and the apparent surface tension, with a charge repulsion acting in the opposite direction to the surface minimization due to the surface tension.

Surface charge can counter the surface tension preventing high pressure within the nanobubbles. It may be expected that as the nanobubble shrinks, the charge density will increase. The effect of charges at the liquid/gas interface is that, the surface negative charges repelling each other are stretching out the surface of the bubble. Thus, the effect of the charges is to reduce the effect of the surface tension. The surface tension tends to reduce the surface, whereas the surface charge tends to expand it. Equilibrium will be reached when these opposing forces are equal meaning that $P_{in}=P_{out}$.

$P_{out}$ can be found to be:

$$P_{out}=\phi^2/2D\epsilon_0$$

where $\phi$ represents the surface charge density on the inner surface of the bubble, D represents the relative dielectric constant of the gas bubble, and $\epsilon_0$ represents the permittivity of vacuum.

The inward pressure, $P_{in}$, due to the surface pressure is given from the Laplace equation:

$$P_{in}=4\gamma/d$$

where $\gamma$ represents the surface tension, and d represents the diameter of the bubble. Equalizing these two pressures, one can determine the charge density at different bubble diameters. For example, for nanobubble diameters of 10 nm, 20 nm, 50 nm, 100 nm, and 200 nm, the charge density is 0.14, 0.1, 0.06, 0.04, and 0.03 $e^-/nm^2$. The surface tension reduction contributes to the stability of nanobubbles.

The charge similarity, together with the lack of van der Waals attraction, tends to prevent coalescence of the nanobubbles.

Furthermore, the nanobubbles protect each other from diffusive loss by a shielding effect, effectively producing a back pressure of gas from neighboring bubbles, which may be separated by approximately the thickness of the unstirred layer, which slows the dissolution. The slow dissolution will be even slower than expected due to higher osmotic pressure at the gas/liquid interface, which is also driving the dissolved gas near the interface back to the nanobubble.

An example of a nanobubbler utilizing a nozzle made of a porous carbon-based material is from Anzai Kantetsu (e.g., see, anzaimcs.com/en/main/examplenanobubble.html, which is hereby incorporated by reference herein). There are a number of other suppliers in Japan and the U. S claiming that their method of making nanobubbles is the correct one, however their specifications show that the bubbles are much larger, with diameters in the ten micrometer range and above.

In summary, nanobubbles possess, inter alia, the following properties:
  A. Longevity
      Disappearance of buoyant force
      Physical stability, persistence (nanobubbles generally do not dissolve away)
  B. Interface Composition
      Hydrogen bonds are formed at the nanobubble surface reducing gas diffusivity
  C. Small carrying capacity that results in controlled gas transfer rates
  D. Migration directionality controlled by ultrasonic fields
  E. Nanobubble interfaces can be loaded with surfactants
  F. Delivery of material by induced rupture utilizing ultrasound fields and/or optical plasmonic fields
  G. Seeded nanobubbies can be used as nucleation sites for crystal growth.

Figure 4:
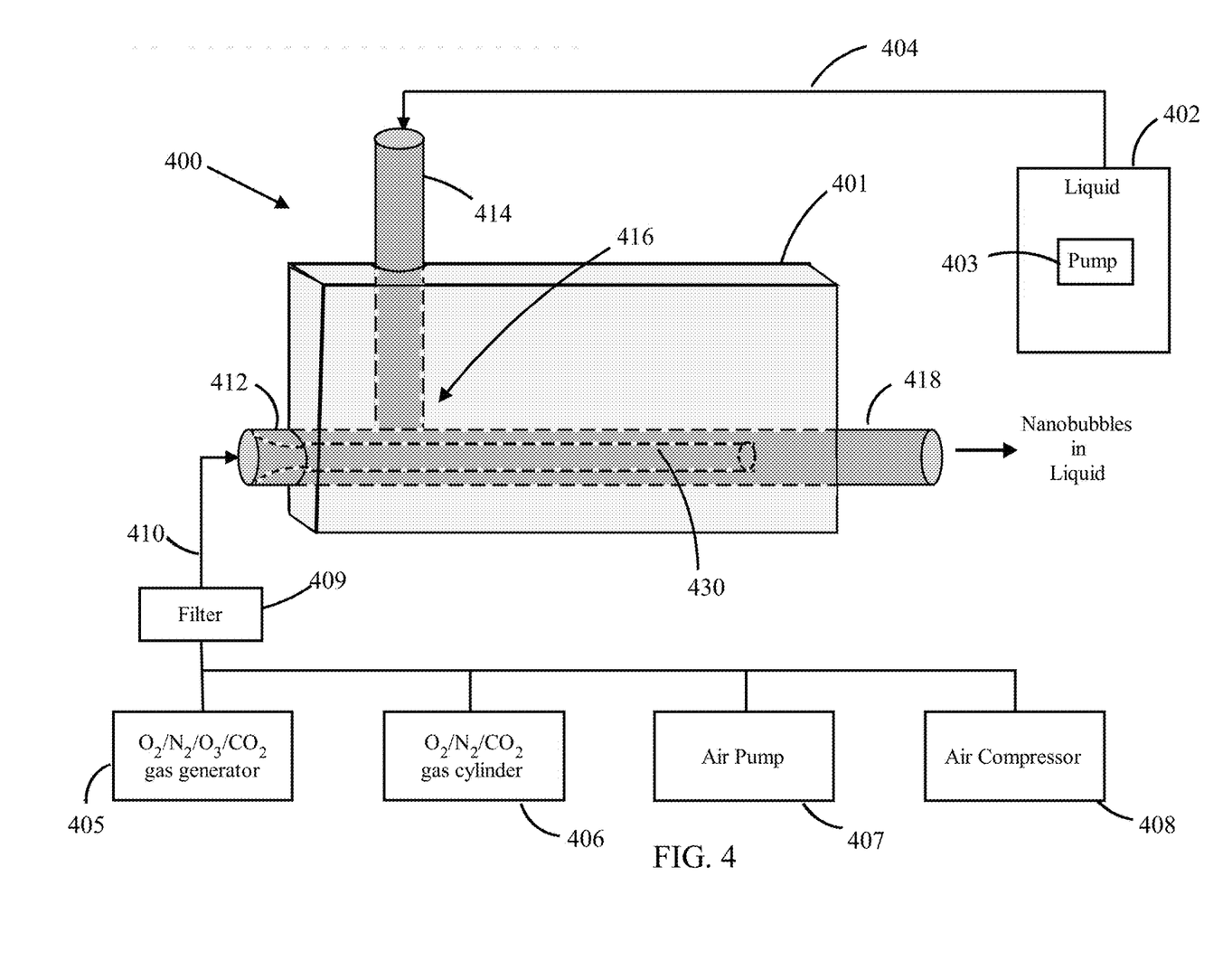
FIG. 4 illustrates an apparatus configured in accordance with embodiments of the present invention.

FIG. 4 illustrates a block diagram of an apparatus 400 (also referred to herein as a nanobubble generator) configured to generate nanobubbles in a liquid using a nanobubbler 401. The nanobubbles may contain any one or more desired gasses (e.g., oxygen ($O_2$), nitrogen ($N_2$), $CO_2$, $O_3$, air, and/or any other desired gas), which may be received from a source, such as from one or more of a gas generator 405 configured to supply such gass(es), one or more pressurized gas cylinders 406 (or from a cylinder that contains a compatible combination of such desired gasses), an air pump 407, and/or an air compressor 408. The supplied gas may be filtered by a filter 409 before being supplied to the nanobubbler 401 at a first inlet 412. An appropriate liquid may be contained within a receptacle 402, and a pump 403 utilized to pump the liquid over the supply line 404 to a second inlet 414. Mixing of the gas and the liquid is then commenced at the juncture 416. In accordance with embodiments of the present invention, a nozzle 430 may be concentrically positioned inside of the pipe 418 for injection/infusing of the gas into the liquid to generate the nanobubbles. The nozzle may be made of a porous carbon-based material. The nanobubbles are generated in the liquid as the liquid passes by and around the nozzle 430. The liquid with the generated nanobubbles then exits from the pipe 418, where it can then be utilized for the various applications described herein (e.g., medical, therapeutic, cosmetic, etc.).

Note that the apparatus 400 may include a plurality of nanobubblers 401, each configured to generate nanobubbles in the liquid containing a different type of gas (e.g., oxygen ($O_2$), nitrogen ($N_2$), $CO_2$, $O_3$, air, and/or any other desired gas). The liquid may be pumped through a combination of such plurality of nanobubblers 401, and then the liquid combined as it exits from each nanobubbler 401 for resulting contact with a person's skin. Alternatively, a single nanobubbler 401 may be configured to generate nanobubbles in the liquid with a plurality of different gasses (e.g., oxygen ($O_2$), nitrogen ($N_2$), $CO_2$, $O_3$, air, and/or any other desired gas), whereby either the different plurality of gasses are simultaneously passed through the nozzle 430, or in an intermittent basis, one after the other.

Figure 5:
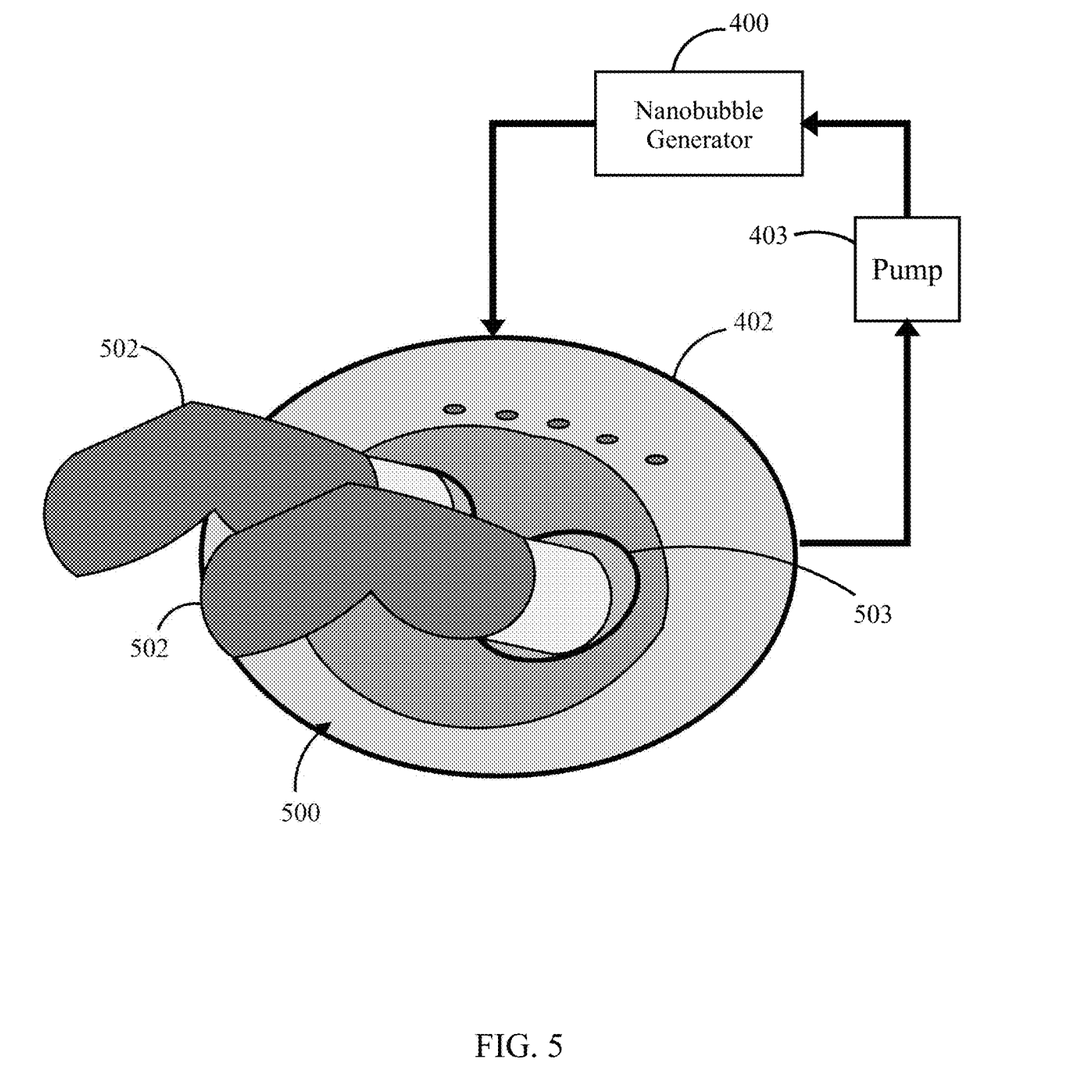
FIG. 5 shows an exemplary apparatus configured in accordance with embodiments of the present invention.

As has been disclosed herein, and as will be further described with respect to FIG. 5, the liquid containing the generated nanobubbles may be delivered to an area of the skin that is affected by some ailment (e.g., diabetic peripheral neuropathy) that can benefit from a cutaneous uptake of the nanobubbles into the skin.

Exemplary Non-Limiting Nanobubbler Apparatus Specifications (e.g., see Anzai Kantetsu previously referenced):
Dimensions: 100×50×20 (mm)
Gas flow: 60 cc/min. (max)
Water flow: 5 L~20 L/min
Nozzle: ϕ 9 mm×65 mm
Gas tube outer diameter: ϕ 6 mm
Body case material: Transparent PVC
Piping outer diameter: ϕ 18 mm Note that such specifications for a nanobubbler may be dependent upon the particular gas, or gasses, to be contained within the generated nanobubbles, and also dependent upon the viscosity of the liquid within which the nanobubbles are generated.

Alternatively, in accordance with embodiments of the present invention, the nanobubbler may be configured in a similar manner as the nanobubbler disclosed in U.S. provisional patent application Ser. No. 62/551,356, which is hereby incorporated by reference herein.

For example, referring to FIG. 5, there is depicted an exemplary device 500 incorporating the apparatus 400 of FIG. 4, which can be configured to supply nanobubbles of $CO_2$ and/or oxygen to the bottom of the feet 502 inserted into locations 503 of the device 500 into which the liquid containing the generated nanobubbles are contained for contact with the skin of the person, resulting in significant improvements for people suffering from diabetic neuropathy as described herein. The $CO_2$ gas in such generated nanobubbles will be as beneficial, or more so, as the $CO_2$ in hot springs for lowering the blood pressure by enlarging the blood vessels. An enlargement of the blood vessels near the skin of the bottom of the feet, will thus be very helpful for delivering more oxygen and nutrients in the same location (in addition to the Bohr effect triggered by the $CO_2$). Furthermore, by supplying nanobubbles of oxygen into the skin, the nerves will be supplied with oxygen directly.

In a non-limiting example in accordance with an embodiment of the present invention, the device 500 may be configured similarly to foot massagers that one can find at many stores such as Target or Bed Bath and Beyond, and modified to incorporate the apparatus 400 as disclosed herein, Naturally, the exemplary device 500 may be configured so that the nanobubble generator 400 and pump 403 are integrally incorporated within the enclosure of the device 500.

Additionally, FIG. 5 is not to be considered as a limiting configuration for utilization of the present invention. The device 500 may have any suitable physical configuration for enabling contact between a liquid containing nanobubbles and a person's skin (or any biological skin), such as a full-body spa, a hot tub, a bathtub, a walk-in bathtub, a hand-held device that can be manipulated to bring such a liquid in contact with the skin (e.g., a well-known wound irrigation tool, etc.). Additionally, embodiments of the present invention are applicable to any method by which nanobubbles containing a gas, or gasses, are generated in a liquid, or any other solution or material described herein, and then placed in contact with the skin.

In addition to the foregoing disclosure, it should be noted that the human skin acts as a protective barrier to keep noxious substances out of the body and prevent excessive loss of water from the internal organs. Strategies have been developed to deliver drugs to the skin and surpass the skin's barrier properties. Consequently, there are many applications related to transdermal and topical drug delivery (e.g., see D. I. J. Morrow et al., "Innovative Strategies for Enhancing Topical and Transdermal Drug Delivery," The Open Drug Delivery Journal, 2007, vol. 1, pp. 36-59).

Based on the examples previously disclosed herein, cutaneous external applications of gases (such as oxygen, carbon dioxide, ozone, etc) may have very positive effects on the health of human beings in the same way as transdermal drug delivery. A critical factor in drug delivery, for example, is the permeability through the skin (e.g., see R. J. Scheuplein, "Permeability of the Skin: A Review of Major Concepts and Some New Developments," The Journal of Investigative Dermatology, vol. 67, issue 5, part 2, pp. 619-681, November 1976), and lately, penetration enhances were developed in particular for drug delivery systems.

In accordance with embodiments of the present invention, methods and devices utilizing a cutaneous external application of gases may implement penetration enhancers (also referred to herein as skin penetration agents) for the specific gases utilized such that an improved transdermal delivery can be achieved.

As previously noted, human skin has the unique property of functioning as a physiochemical barrier; however, especially small molecules can surpass this barrier by being able to pass through the cortical layer, which is considered to form the main deterrent. In the publication J. D. Bos et al., "The 500 Dalton rule for the skin penetration of chemical compounds and drugs," Exp. Dermatol, vol. 9, pp, 165-169, July 2000, it was asserted that the molecular weight of a compound must be under 500 Dalton to allow skin absorption. Larger molecules cannot pass the corneal layer. As a result, the most commonly used pharmacological agents applied in topical dermatological therapy drug delivery systems are under 500 Dalton (the 500 Dalton rule). For example, nanobubbles of oxygen and carbon dioxide easily fulfill this rule (oxygen having 32 Dalton and $CO_2$ having 44 Dalton).

As previously disclosed, gas nanobubbles can be supplied externally to the skin in a number of ways, such as when they are embedded in liquids, gels, ointments, creams, etc. In accordance with certain embodiments of the present invention, their effectivity may be improved with implementation of a skin penetration enhancement, be it physical or chemical (e.g., see H. Trommer et al., "Overcoming the Stratum Corneum: The Modulation of Skin Penetration," Skin Pharmacol. Physiol., vol. 19, pp. 106-121, May 9, 2006). The main lipids in the stratum corneum are ceramides such as fatty acids and cholesterol. Gas nanobubbies supplied to the human skin, as stated above, can have an important function if, in addition to their small sizes on the order of magnitude smaller than that of the skin pores, they are embedded in formulations with skin penetration enhancers.

The nanobubbles permeation options include sweat ducts and hair follicles, which can function as diffusion shunts with relatively easy pathways to the stratum corneum. However, other options for nanobubbles permeation are through the transepidermal route and the route via pores. The transepidermal route can be divided into the transcellular and intercellular route, whereby the more direct route is the transcellular, but the more common route for nanobubbles to penetrate the skin is the intercellular route (e.g., see J. Hadgraft, "Skin deep," Int. J. Pharm. Investig., 1(1), pp. 4-9, Jan.-Mar. 2011).

There are many substances that can improve the nanobubbles gas permeation, for example dimethylsuphoxide, pyrolidones, etc. (e.g., see J. Hadgraft et al., "Transdermal Drug Delivery: Developmental Issues and Research Initiatives," Marcel Dekker, 1989), but at least some of the properties of a penetration enhancer are that it should be non-toxic, non-irritant, and non allergenic; it should not illicit any pharmacological activity within the body; it should be compatible and stable with the other components in the formulation, such as the vehicle for transporting the nanobubbles; it should not enhance the loss of substances from the body; the skin barrier integrity should recover rapidly; it should not be expensive; and it should be acceptable in terms of odor, color, and texture.

For example, hydration fatty acids fulfill the properties above (as long they are not used in concentrations that may irritate the skin). Fatty acids are carboxylic acids often with long unbranched aliphatic tails. Examples are lauric acid, linoleic acid, and oleic acid. Generally, unsaturated fatty acids possess a configuration that is more effective as a skin penetrator. In this configuration, a "kink" into the alkyl tail is introduced, and as a result, this configuration causes a greater disruption to the lipid layers. Furthermore, the length of the tail is also significant whereby C10 and C12 carbon chain lengths provide the greatest permeation enhancement (e.g., see B. J. Aungst et al., "Enhancement of naloxone penetration through human skin in vitro using fatty acids, fatty alcohols, and caffeine," J. Pharmaceut. 1986; 33: pp. 255-34).

For example, oleic acid is a "kinked" fatty acid, and has a long C18 tail. It was proven by thermal analysis that the action of oleic acids disrupts the intercellular lipid packing, which was also proved using electron microscopy.

As a result, and as an example, a formulation that includes the gas nanobubbles vehicle (e.g., a liquid, such as water, oil, saline, a film, a gel, a cream, a lotion, an aerosol, or an ointment), combined with hydration agents and oleic acids, can be a suitable formulation to optimize the nanobubble gas permeation through the stratum corneum. Another agent that can be very helpful to enhance the skin permeability are alcohols among the polyvalent alcohols; propylene glycol has co-solvent properties and may have a synergetic action in a mixture with oleic acids. These agents can be combined together, used individually, or in partial mixtures (e.g., see H. Trommer et al., previously referenced herein).

The skin can be considered to be a composite diffusion media corresponding to stratum corneum, epidermis, and a thin layer of dermis, each with its corresponding diffusion coefficient and thickness. This overlays the blood stream, which has a flow that can also affect the diffusional resistance (e.g., see R. J. Scheuplein, previously referenced herein).

Some of the gases available for creating nanobubbles in a vehicle can have a strong action against bacteria, viruses, and fungi, and can exercise significant antimicrobial activity. As previously disclosed, application of ozone nanobubbles has a therapeutic window; if the ozone nanobubbles are applied in a low concentration, they have little therapeutic effect, while higher concentrations can be toxic and irritating. In practice, the ozone nanobubbles may be applied together with oxygen nanobubbles reducing the respiratory exposure to ozone. Ozone has a relatively short lifetime, and when administered, must be produced at the point of use. In particular, ozone, due to its actions on wound pathogens, is very helpful when due to poor blood circulation and neuropathy, diabetic foot lesions result (e.g., see G. V. Sunnen, "Diabetic Wound Management: A Key Ingredient is Missing," March 2007, 10 pages).

Within other embodiments of the present invention, administration of gas nanobubbles with a contained medication, or as gas nanobubbles with a contained medication in a liquid, can be performed by incorporating them into capsules, a spray, ointments, pills, lotions, and so on.

Administration of gas nanobubbles with a contained medication can be performed by incorporating them into capsules/pills/tablets, which are then taken by mouth through the GI system so that there is an uptake through the kidney and/or liver to be absorbed into the blood stream. Other more rapid administration of such medication contained within gas nanobubbles, for example, can be by sublingual and buccal methods. Sublingual administration involves placing a drug, a pill, a capsule, etc. under the tongue to be absorbed into the blood through the tissue there. Buccal administration involves a drug, a pill, a capsule, etc. administered between the gums and cheek where it dissolves and is absorbed into the blood stream. Both methods may come in the form of capsules, tablets, films, sprays, lozenges, etc. Gas nanobubbles can also be supplied by these methods with therapeutic effects. For example, direct delivery of oxygen, $CO_2$, and others into the blood stream. Other drug delivery methods can be adjusted to deliver gas nanobubbles including for example administration through the skin.

While the following terms are believed to be well understood by one of ordinary skill in the art, the following definitions are set forth to facilitate explanation of the presently disclosed subject matter. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims. Unless otherwise indicated, all numbers expressing quantities of ingredients, reaction conditions, and so forth used in the specification and claims are to be understood as being modified in all instances by the term "about," Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments +10%, in some embodiments ±5%, in some embodiments ±1%, in some embodiments ±0.5%, and in some embodiments +0.1% from the specified amount, as such variations are appropriate to perform the disclosed method.

As used herein, "significance" or "significant" relates to a statistical analysis of the probability that there is a non-random association between two or more entities. To determine whether or not a relationship is "significant" or has "significance," statistical manipulations of the data can be performed to calculate a probability, expressed as a "p value,". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

It will be understood that particular embodiments described herein are shown by way of illustration and not as limitations of the invention. The principal features of this invention can be employed in various embodiments without departing from the scope of the invention.

All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or" Throughout this application, the terms "about" or "approximately" are used to indicate that a value includes the inherent variation of error for the device, the method being employed to determine the value, or the variation that exists among the study subjects.

What is claimed is:

1. A method comprising:
generating gas nanobubbles in a liquid with a nanobubbler comprising a gas nozzle made of a porous ceramic material, wherein the porous ceramic material does not include any carbon; and
contacting the liquid containing the gas nanobubbles with a person's skin, wherein the contacting of the liquid containing the gas nanobubbles with the person's skin results in a cutaneous uptake of a gas contained in the gas nanobubbles.

2. The method as recited in claim 1, wherein the gas is selected from the group consisting of oxygen, carbon dioxide, ozone, nitrogen, hydrogen, environmental air, and any combination thereof.

3. The method as recited in claim 1, wherein the liquid is selected from the group consisting of water, oil, saline, a gel, a cosmetic cream, a lotion, an aerosol, and an ointment.

4. The method as recited in claim 1, wherein the liquid has a viscosity in a range greater than 100,000 cP.

5. The method as recited in claim 1, wherein the gas nanobubbles comprise nanobubbles containing oxygen and nanobubbles containing carbon dioxide, wherein the contacting of the liquid containing the gas nanobubbles with the person's skin comprises alleviating nerve numbness associated with peripheral neuropathy.

6. The method as recited in claim 5, wherein the contacting of the liquid containing the gas nanobubbles with the person's skin comprises alleviating symptoms associated with peripheral neuropathy through a penetration of the gas nanobubbles containing carbon dioxide sufficiently deep into the dermis to dilate the blood vessels that supply peripheral nerves and a supply of the gas nanobubbles containing oxygen to the nerves.

7. The method as recited in claim 1, wherein the liquid further comprises a skin penetration agent configured to enlarge pores in the person's skin.

8. The method as recited in claim 7, wherein the skin penetration agent is selected from the group consisting of dimethylsuphoxide, pyrolidones, lauric acid, linoleic acid, oleic acid, and any combination thereof.

9. The method as recited in claim 1, wherein an average diameter of at least some of the gas nanobubbles is less than 100 nanometers.

10. The method as recited in claim 1, wherein the gas nanobubbles contain a pharmaceutical medication, and wherein contacting the liquid containing the gas nanobubbles with a person's skin comprises either a sublingual or buccal administration.

11. The method as recited in claim 1, wherein the liquid has a viscosity in a range greater than 600,000 cP.

12. The method as recited in claim 1, wherein the contacting of the liquid containing the gas nanobubbles with the person's skin is performed without applying the liquid through a break in the person's skin.

13. The method as recited in claim 1, wherein an average diameter of the gas nanobubbles is less than 200 nanometers.

14. The method as recited in claim 1, wherein an average diameter of the gas nanobubbles is less than 90 nanometers.

15. The method as recited in claim 1, wherein the gas nanobubbles contain oxygen, and wherein an average diameter of at least some of the gas nanobubbles is sufficiently small so that the oxygen is directly permeable through the person's skin to nerves in a dermis of the person's skin.

16. A method comprising:

generating gas nanobubbles in a liquid; and contacting the liquid containing the gas nanobubbles with a person's skin, wherein the contacting of the liquid containing the gas nanobubbles with the person's skin results in a cutaneous uptake of a gas contained in the gas nanobubbles, wherein the liquid has a viscosity in a range greater than 600,000 cP, wherein the liquid having a viscosity in a range greater than 600,000 cP was infused with the gas nanobubbles by increasing a temperature of the liquid in order to lower its viscosity.

* * * * *